(12) United States Patent
Shimizu

(10) Patent No.: US 7,278,965 B2
(45) Date of Patent: Oct. 9, 2007

(54) OPERATING MECHANISM FOR MEDICAL DEVICE

(75) Inventor: Masami Shimizu, Tokyo (JP)

(73) Assignee: Olympus Corporation (JP)

( * ) Notice: Subject to any disclaimer, the term of this patent is extended or adjusted under 35 U.S.C. 154(b) by 379 days.

(21) Appl. No.: 10/789,200

(22) Filed: Feb. 26, 2004

(65) Prior Publication Data
US 2004/0171912 A1    Sep. 2, 2004

(30) Foreign Application Priority Data
Feb. 27, 2003    (JP)    ............... 2003-051853

(51) Int. Cl.
*A61B 1/045*    (2006.01)

(52) U.S. Cl. .............. 600/118; 600/112; 600/133; 335/205

(58) Field of Classification Search .......... 600/112, 600/118, 133, 134; 606/1, 42; 335/205, 335/207
See application file for complete search history.

(56) References Cited

U.S. PATENT DOCUMENTS

| | | | | |
|---|---|---|---|---|
| 3,273,091 | A * | 9/1966 | Wales, Jr. ............... | 335/207 |
| 4,025,885 | A * | 5/1977 | Giannini ................. | 335/154 |
| 4,288,767 | A * | 9/1981 | Lee ....................... | 335/6 |
| 4,751,485 | A * | 6/1988 | Fujio et al. ............. | 335/206 |
| 4,812,804 | A * | 3/1989 | Masaki ................... | 338/200 |
| 4,982,726 | A * | 1/1991 | Taira ...................... | 600/158 |
| 5,701,200 | A * | 12/1997 | Horton .................... | 359/435 |
| 6,246,307 | B1 * | 6/2001 | Friedman ................ | 335/205 |
| 6,590,763 | B2 * | 7/2003 | Kishimoto .............. | 361/683 |
| 6,633,438 | B2 * | 10/2003 | Anhalt .................... | 359/694 |
| 6,929,602 | B2 * | 8/2005 | Hirakui et al. .......... | 600/159 |
| 2003/0090352 | A1 * | 5/2003 | Lee et al. ............... | 335/202 |
| 2004/0210108 | A1 * | 10/2004 | Shimizu et al. ......... | 600/112 |
| 2004/0230214 | A1 * | 11/2004 | Donofrio et al. ........ | 606/169 |
| 2005/0059858 | A1 * | 3/2005 | Frith et al. .............. | 600/118 |

FOREIGN PATENT DOCUMENTS

| | | | |
|---|---|---|---|
| FR | 2451093 | * | 3/1980 |
| JP | 2000-139819 | | 5/2000 |
| WO | WO97/16123 | | 5/1997 |

* cited by examiner

*Primary Examiner*—John P. Leubecker
(74) *Attorney, Agent, or Firm*—Ostrolenk, Faber, Gerb & Soffen, LLP

(57) ABSTRACT

An operating mechanism for a medical device comprises a photo-interrupter that can designate specified functional operations, an air-tight unit that can accommodate this photo-interrupter air-tightly, a moving member which is disposed inside the air-tight unit, and which moves between a position in which the photo-interrupter designates an operation and a position in which the photo-interrupter does not designate an operation, a coil spring which directly or indirectly biases the moving member to the position in which no operation is designated, an operating member which is disposed on the outside of the air-tight unit, and which can be operated by an operator, and a pair of magnets which transmit a magnetic force that moves the moving member into the position in which an operation is designated against the elastic force of the coil spring in accordance with the operation of the operating member.

14 Claims, 14 Drawing Sheets

OPERATING MECHANISM FOR MEDICAL DEVICE

This application claims benefit of Japanese Application No. 2003-51853 filed on Feb. 27, 2003, the contents of which are incorporated by this reference.

BACKGROUND OF THE INVENTION

1. Field of the Invention

The present invention relates to an operating mechanism for a medical device which is used to perform functional operations by a switching operation, and which is suitable for use in medical devices that are sterilized in an autoclave.

2. Description of the Related Art

In recent years, autoclave sterilization using high-temperature high-pressure steam has become popular as a method for sterilizing medical devices such as endoscopes and the like.

Generally, remote switches used for functional operations such as endoscopic image brightness adjustment, endoscopic image freeze designation, focus adjustment of the endoscope or the like are installed in electronic endoscopes that allow observation or treatment inside body cavities by the insertion of a long slender insertion part into such body cavities, and endoscopic imaging devices that are detachably attached to the ocular part of the endoscope and that capture endoscopic images.

An endoscope in which an optical lens inside an air-tight unit that is not permeated by steam even in the case of autoclave sterilization is moved by the operation of a remote switch located outside this air-tight unit so that the focal point is adjusted is described in Japanese Patent Application Laid-Open No. 2000-139819 as one example of an autoclave-sterilizable endoscope that has such a remote switch.

SUMMARY OF THE INVENTION

The operating mechanism for a medical device that is provided by the present invention comprises switching means that can designate specified functional operations, an air-tight unit that can accommodate the switching means air-tightly, a moving member which is disposed inside the air-tight unit, and which moves between a position where an operation is designated by the switching means and a position where no operation is designated, biasing means which directly or indirectly biases the abovementioned moving member to the position where no operation is designated, an operable member which is disposed outside the air-tight unit, and which can be operated by an operator, and switching-function change-over means which moves the moving member by magnetic force against the biasing force of the biasing means to the position where an operation is designated in accordance with the operation of the operating member. Accordingly, the switching means accommodated inside the air-tight unit is not exposed to high-temperature high-pressure steam during autoclave sterilization. Furthermore, as a result of the moving member being moved by the switching-function change-over means, the switching means can be switched between a state in which an operation is designated and a state in which no operation is designated.

The above and other objects, features and advantages of the invention will become more clearly understood from the, following description referring to the accompanying drawings.

BRIEF DESCRIPTION OF THE DRAWINGS

FIG. 1 is a side view of the overall endoscopic apparatus;

FIG. 2 is a sectional view of the endoscopic image pickup apparatus;

FIG. 3 is a sectional view which shows the remote switch prior to the switching operation;

FIG. 4 is a sectional view which shows the remote switch during the switching operation;

FIG. 5 is a plan view which shows the photo-interrupter prior to the switching operation;

FIG. 6 is a plan view which shows the photo-interrupter during the switching operation;

FIG. 7 is a sectional view which shows the remote switch prior to the switching operation;

FIG. 8 is a sectional view which shows the remote switch during the switching operation;

FIG. 9 is a sectional view which shows the remote switch prior to the switching operation;

FIG. 10 is a sectional view which shows the remote switch during the switching operation;

FIG. 11 is a sectional view which shows the remote switch prior to the switching operation;

FIG. 12 is a sectional view which shows the remote switch during the switching operation;

FIG. 15 is a sectional view of the endoscopic image pickup apparatus;

FIG. 16 is a plan view of the printed circuit board;

FIG. 17 is a sectional view of the endoscopic image pickup apparatus;

FIG. 18 is a perspective view of the first resin member;

FIG. 19 is an explanatory diagram which shows the internal structure of the second resin member;

FIG. 20 is a sectional view which shows the remote switch prior to the switching operation;

FIG. 21 is a sectional view which shows the remote switch during the switching operation; and FIG. 22 is a sectional view along line 22-22 shown in FIG. 20.

DETAILED DESCRIPTION OF THE PREFERRED EMBODIMENTS

Embodiments of the present invention will be described below with reference to the attached figures.

A first embodiment of the present invention will be described with reference to FIGS. 1 through 6.

Figure 1:
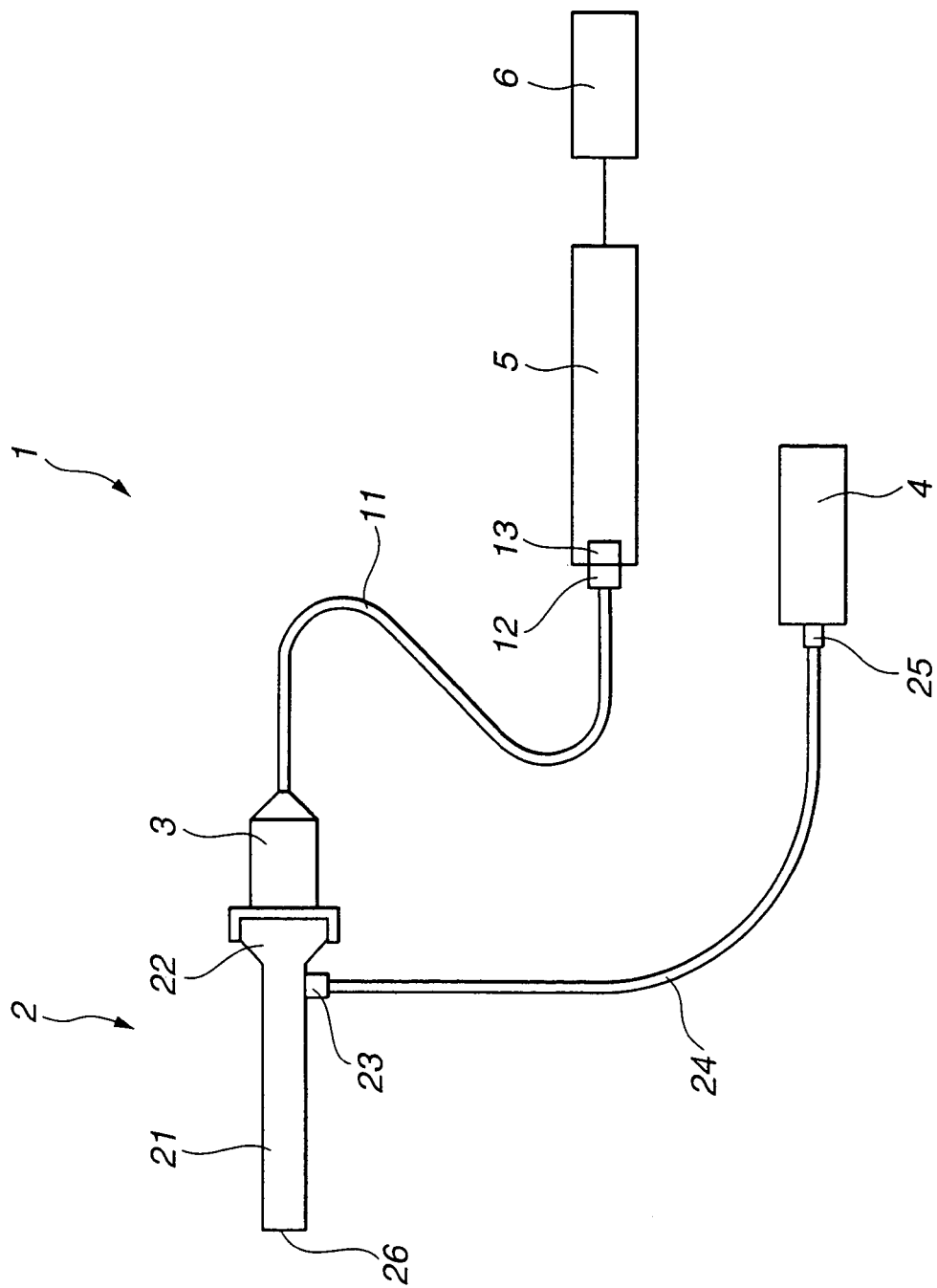
FIGS. 1 through 6 are figures that illustrate a first embodiment of the present invention.

As is shown in FIG. 1, the endoscopic apparatus 1 is constituted mainly by an endoscope 2, an endoscopic image pickup apparatus 3, a light source apparatus 4, a video processor 5 and a monitor 6.

The endoscopic image pickup apparatus 3 is detachably mounted on the endoscope 2. The light source apparatus 4 supplies illuminating light to the endoscope 2. The video processor 5 performs signal processing for the endoscopic image pickup apparatus 3. The monitor 6 displays video signals that are output from the video processor 5.

The endoscope 2 has an insertion part 21, an ocular part 22 and a mounting base 23. The ocular part 22 is formed on the base end of the insertion part 21. The mounting base 23 is disposed on the side part of the endoscope 2. One end of a light guide cable 24 is connected to the mounting base 23. A connector 25 is disposed on the other end of this light guide cable 24. The connector 25 is detachably connected to the light source apparatus 4.

A light guide and a relay optical system not shown in the figures are disposed inside the endoscope 2. An illumination window and an observation window not shown in the figures are formed in the tip end surface 26 of the insertion part 21. An ocular lens not shown in the figures is disposed on the base end-side of this observation window.

Figure 2:
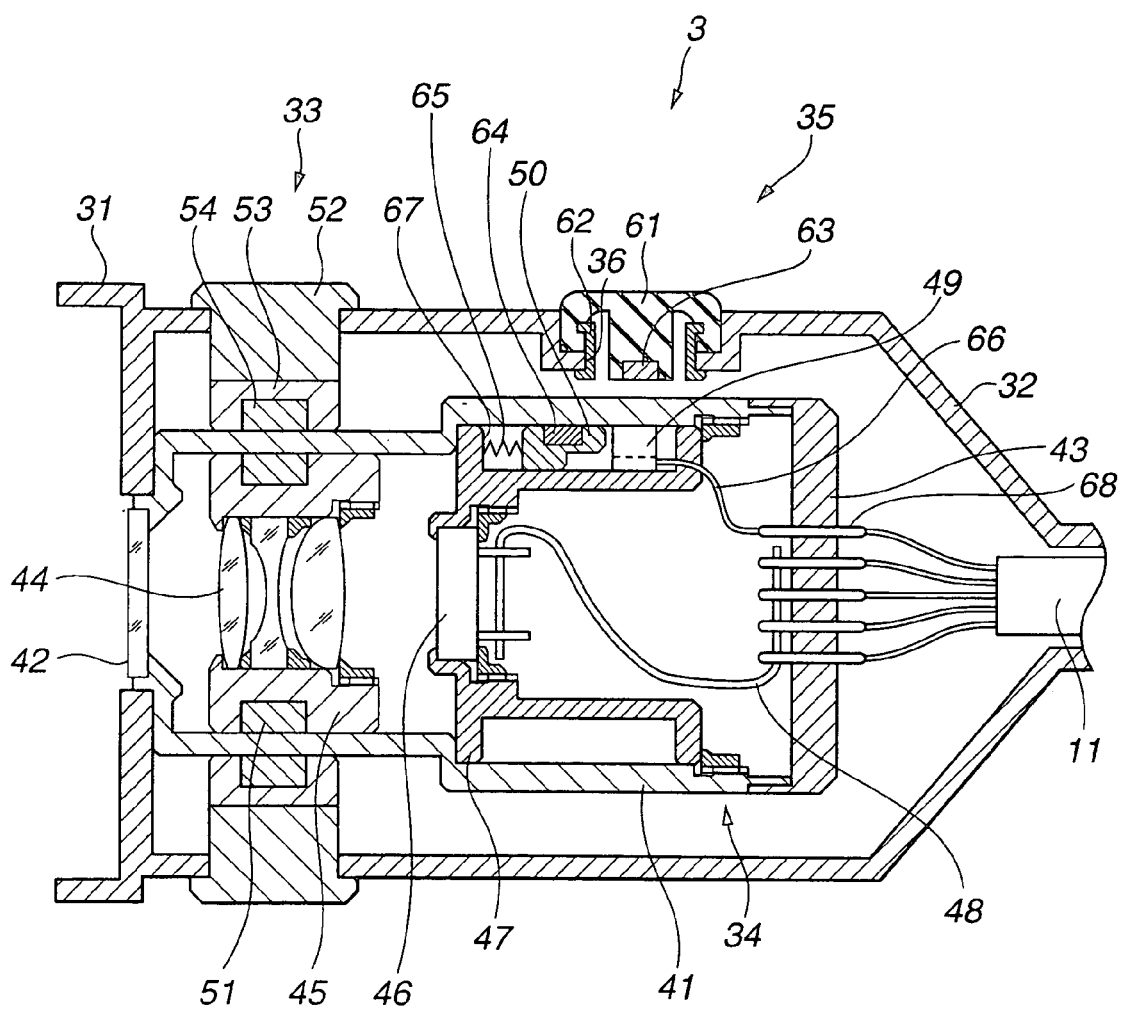

An ocular lens not shown in the figures is disposed in the ocular part 22. The endoscopic image pickup apparatus 3 is detachably mounted on the ocular part 22. The solid state image pick up element 46 shown in FIG. 2 is contained in this endoscopic image pickup apparatus 3 as an image pickup element. As is shown in FIG. 1, a camera cable 11 extends from the endoscopic image pickup apparatus 3. A plug 12 is disposed on the end part of the camera cable 11. A receptacle 13 is disposed on the video processor 5. The plug 12 is detachably connected to the receptacle 13.

The connector 25 of the light guide cable 24 is connected to the light source apparatus 4. As a result, illuminating light emitted from a lamp (not shown in the figures) inside the light source apparatus 4 is directed onto the end surface of the light guide cable 24. Consequently, the illuminating light is transmitted by this light guide cable 24 and supplied to the light guide inside the endoscope 2. The illuminating light that is supplied to the light guide inside the endoscope 2 is emitted toward the front from the illumination window disposed in the tip end surface 26 of the insertion part 21. As a result, the subject is illuminated.

An optical image of the subject illuminated by the illuminating light passes through the observation window in the tip end surface 26 and an object lens, and is focused; this image is transmitted to the side of the ocular part 22 by the-relay optical system. As a result, the subject can be observed via an ocular lens not shown in the figures.

The optical images that are transmitted to the ocular part 22 are captured by the solid state image pickup element 46 of the endoscopic image pickup apparatus 3 shown in FIG. 2.

As is shown in FIG. 1, the endoscopic image that is captured by the solid state image pickup element 46 is transmitted to the video processor 5 via the camera cable 11 that extends from the endoscopic image pickup apparatus 3, the plug 12 and the receptacle 13.

The construction of the endoscopic image pickup apparatus 3 will be concretely described with reference to FIG. 2.

As is shown in this figure, the endoscopic image pickup apparatus 3 is constituted mainly by a scope-mount 31, a case body 32, a focus adjustment part 33, an air-tight unit 34, a remote switch 35, a camera cable 11 and the plug 12 shown in FIG. 1.

The scope mount 31 is formed so that this mount is detachable with respect to the ocular part 22 of the endoscope 2 shown in FIG. 1.

The remote switch 35 is an operating mechanism that can be operated by an operator.

The air-tight unit 34 has a structure in which a cover glass 42 is joined to one end of an air-tight unit main body 41, and a hermetic connector 43 is joined to the other end of this air-tight unit main body 41. As a result of this structure, the interior of the air-tight unit 34 is completely air-tight.

An optical system 44, a lens frame 45, a solid state image pickup element 46, a solid state image pickup element frame 47, a flexible board 48 (for example) constituting signal transmission means, a photo-interrupter 49 and a moving member 50 are disposed inside the air-tight unit 34.

The optical system 44 has a plurality of optical lenses, and is disposed on the rear side of the cover glass 42. This optical system 44 further transmits the endoscopic images transmitted to the ocular part 22 of the endoscope 2 shown in FIG. 1, and focuses these images on the imaging plane of the solid state image pickup element 46.

The plurality of optical lenses and the like that constitute the optical system 44 are disposed in the lens frame 45. This lens frame 45 can slide in the direction of the optical axis of the optical system 44 in a state in which the lens frame 45 is in contact with the inner circumference of the air-tight unit main body 41. Lens frame magnets 51 are disposed on portions of the outer circumference of this lens frame 45.

The solid state image pickup element 46 is disposed on the tip end of the solid state image pickup element frame 47. The solid state image pickup element frame 47 is disposed on the rear side of the lens frame 45, and is fastened to the inner circumference of the air-tight unit main body 41.

For example, the solid state image pickup element 46 is constituted by a charge-coupled device (CCD); this element captures the endoscopic images that are transmitted by the optical system 44 and subjects these images to a photoelectric conversion. The electrical signals produced by the photoelectric conversion performed by this solid state image pickup element 46 are transmitted to the hermetic connector 43 via the flexible board 48.

The photo-interrupter 49 constitutes switching means. The moving member 50 is disposed so that this moving member advances and retracts between a light emitting part 71 and light receiving part 72 (shown in FIGS. 5 and 6 described later) disposed in the photo-interrupter 49.

The focus adjustment part 33 is constituted mainly by a focus ring 52 and a moving part 53. The focus ring 52 is disposed on the case body 32 so that this focus ring can rotate. The outer circumferential surface of this focus ring 52 is exposed from the case body 32.

The moving part 53 is formed in a ring shape. This moving part 53 is disposed on the side of the inner circumferential surface of the focus ring 52. The moving part 53 is mounted on the front side of the air-tight unit main body 41. Focusing magnets 54 are mounted on portions of the inner circumference of the moving part 53 so that these focusing magnets 54 face the lens frame magnets 51 with the air-tight unit main body 41 interposed.

A cam mechanism or the like not shown in the figures is disposed between the focus ring 52 and the moving part 53. This mechanism is constructed so that the moving part 53 can be moved in the direction of the optical axis by rotating this focus ring 52. When this moving part 53 is moved, the lens frame 45 is caused to move by the magnetic connecting force between the focusing magnets 54 and the lens frame magnets 51. As a result, the focus of the optical system 44 can be adjusted.

Furthermore, an O-ring or the like (not shown in the figures) which prevents unintentional rotation is disposed on the focus ring 52.

The remote switch 35 is constituted mainly by a photo-interrupter 49, a moving member 50, an operating member 61, a fastening member 62, an operating part magnet 63 that constitutes a first magnet, a moving member magnet 64 that constitutes a second magnet, a coil spring 65 (for example) that constitutes biasing means, and a photo-interrupter harness 66.

An opening part 36 is formed in the side surface of the case body 32. The operating member 61 is disposed in this opening part 36.

The operating member 61 is a member which is disposed on the outside of the air-tight unit 34, and which can be operated by an operator. This operating member 61 has a push button shape, and is formed of a material that has elasticity such as a rubber member or the like. The fastening member 62 is fastened to the case body 32 so that the operating member 61 does not fall out.

The operating part magnet 63 is disposed as an integral part of the operating member 61. The operating part magnet 63 is disposed on the side of the surface that faces the air-tight unit 34. The moving member 50 is disposed inside the air-tight unit 34. The moving member magnet 64 is disposed as an integral part of the moving member 50. This moving member magnet 64 is disposed so that this magnet 64 faces the operating part magnet 63 with the air-tight unit main body 41 interposed.

One end of the coil spring 65 is fastened to the moving member 50. This coil spring 65 biases the moving member 50 in the direction that separates the moving member 50 from the photo-interrupter 49. The photo-interrupter harness 66 is disposed on the photo-interrupter 49. This photo-interrupter harness 66 outputs the detection results of the photo-interrupter 49. The other end of the coil spring 65 is fastened to a flange part 67 on the solid state image pickup element frame 47.

Furthermore, the fastening of the coil spring 65 is not limited to the solid state image pickup element frame 47; it is sufficient if this spring is fastened to a part other than the movable part, such as the air-tight unit main body 41 or the-like.

The photo-interrupter harness 66 passes through a through-hole formed in the solid state image pickup element frame 47, and is connected to a contact pin 68 in the hermetic connector 43.

Furthermore, in accordance with the output from the photo-interrupter 49, the video processor 5 shown in FIG. 1 is assigned various types of functional operations such as brightness adjustment of the endoscopic images, freezing of endoscopic images or the like; furthermore, this video processor 5 can be controlled by remote control. Moreover, the number of remote switches 35 is not limited to one; a construction in which a plurality of such switches are provided may also be used.

As a result of the structure described above, the photo-interrupter 49 of the remote switch 35 constitutes switching means that allow the designation of specified functional operations.

The photo-interrupter 49 is can be accommodated air-tightly in the air-tight unit 34. The moving member 50 disposed inside the air-tight unit 34 is constructed so that this member moves between a position that designates the operation of the photo-interrupter 49 (also described as the "operation designating position") and a position that does not designate any operation (also described as the "operation non-designating position").

The coil spring 65 directly biases the moving member 50 so that the moving member 50 is positioned in the operation non-designating position.

The operating part magnet 63 and moving member magnet 64 constitute switching-function change-over means with respect to the photo-interrupter 49, which moves the moving member 50 into the operation designating position against the elastic force of the coil spring 65 in accordance with the operating state of the operating member 61.

In other words, an operating mechanism for a medical device is constituted by the photo-interrupter 49, air-tight unit 34, moving member 50, operating member 61, operating part magnet 63 and coil spring 65.

The operation of the operating mechanism for a medical device constructed as described above will be described next.

Here, it will be assumed that the function of increasing the brightness of the endoscopic images is assigned as the operating function of the remote switch 35 shown in FIG. 2.

As is shown in FIG. 1, the endoscopic image pickup apparatus 3 used for endoscopic examination is attached to the ocular part 22 of the endoscope 2.

The endoscopic images obtained by the endoscope 2 are focused on the solid state image pickup element 46 via the cover glass 42 and optical system 44 shown in FIG. 2. In this solid state image pickup element 46, the endoscopic images are subjected to a photoelectric conversion so that electrical signals are produced. These electrical signals are transmitted to the video processor 5 via the flexible board 48, hermetic connector 43, camera cable 11, plug 12 (shown in FIG. 1) and receptacle 13.

In the video processor 5, video signals are produced from these electrical signals, and these video signals are output to the monitor 6. As a result, endoscopic images are displayed on the screen of the monitor 6.

In cases where the focal point is not properly adjusted in the endoscopic images displayed on the screen of the monitor 6, the focus ring 52 shown in FIG. 2 is operated in order to adjust the focus. When the focus ring 52 is turned, the moving part 53 is caused to move forward or rearward by a mechanism not shown in the figures. In this case, the lens frame 45 also moves forward or rearward in linkage with the movement of the moving part 53 as a result of the magnetic connection between the focusing magnets 54 and lens frame magnets 51. As a result, the focus is adjusted.

Here, the operation of the remote switch 35 will be concretely described using a case in which the endoscopic images displayed on the monitor 6 are to be brightened as an example.

Figure 3:
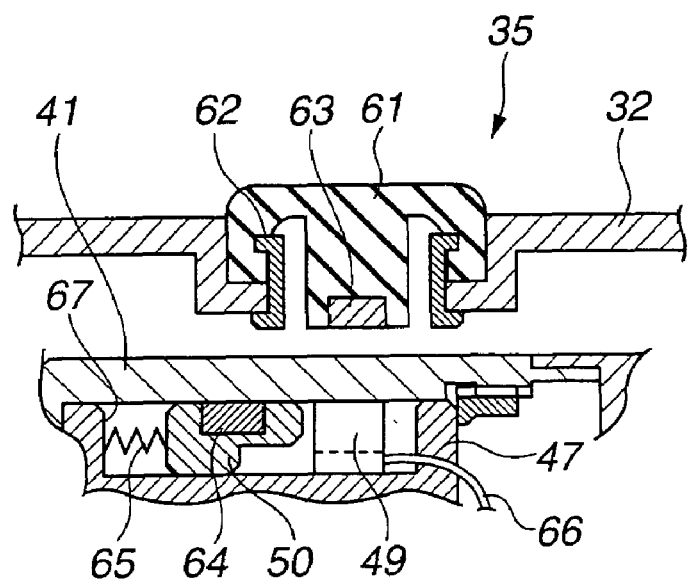
Figure 5:
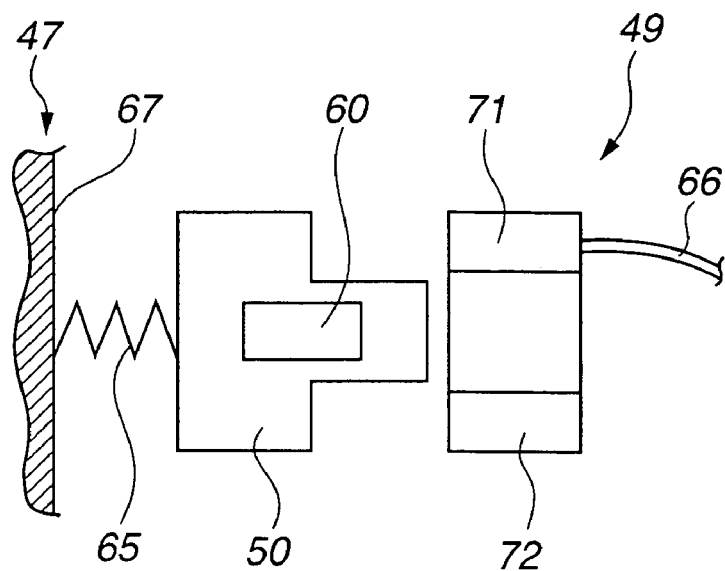

As is shown in FIG. 3, in a state where the operating member 61 is not pressed, the operating part magnet 63 and moving member magnet 64 are separated from each other. Consequently, the moving member 50 is disposed in the operation non-designating position which is on the side of the flange part 67 (on the left side in the plane of the page) as a result of the elastic force of the coil spring 65. Accordingly, as is shown in FIG. 5, there is no obstruction between the light-emitting part 71 and light-receiving part 72 of the photo-interrupter 49. As a result, the output from the photo-interrupter 49 indicates that the moving member 50 has not entered the area between these parts.

Figure 4:
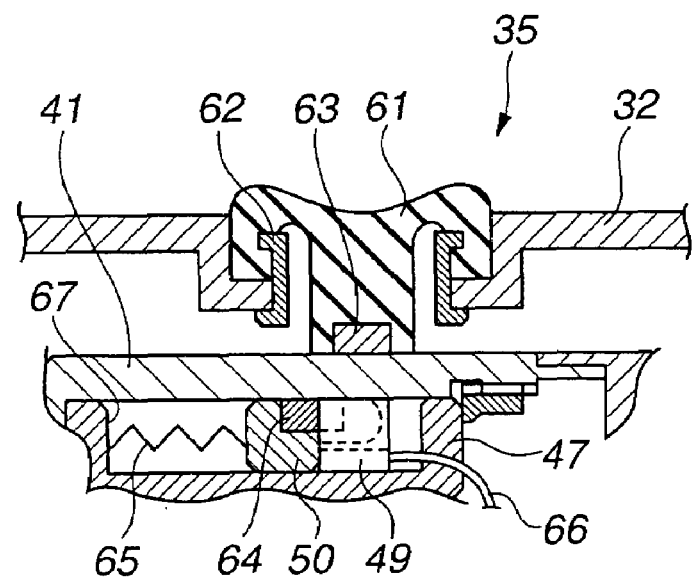
Figure 6:
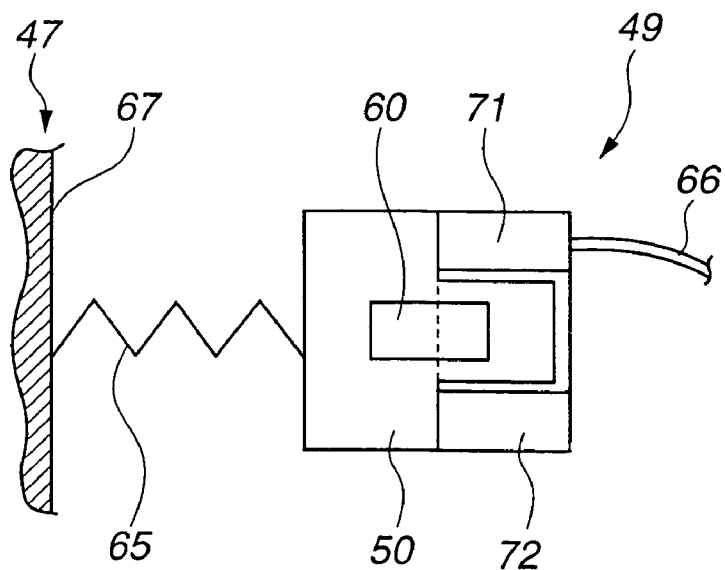

Subsequently, an operation in which the operating member 61 is pressed is performed as shown in FIG. 4. Consequently, the operating part magnet 63 approaches the moving member magnet 64. As a result, a magnetic connecting force is generated between the operating part magnet 63 and the moving member magnet 64, so that the moving member 50 begins to move rightward along the plane of the page against the elastic force of the coil spring 65. Then, the moving member 50 finally enters the area between the light-emitting part 71 and light-receiving part 72 of the photo-interrupter 49 as shown by the broken line in FIG. 4 and as shown in FIG. 6, so that a light-blocking state results.

As a result, the photo-interrupter 49 outputs a signal indicating that light is blocked between the light-emitting part 71 and light-receiving part 72. The signal that is output from this photo-interrupter 49 is transmitted to the video processor 5 via the photo-interrupter harness 66, hermetic connector 43 (shown in FIG. 2), camera cable 11, plug 12 (shown in FIG. 1) and receptacle 13, and is processed, so that the video processor 5 increases the brightness by one step.

Subsequently, if an operation in which the operating member 61 is pressed is again performed, the brightness is further increased by one step by an operation similar to that described above.

Thus, since the photo-interrupter 49 constituting the switching means is disposed inside the air-tight unit 34, deterioration of the switching means of the remote switch can be prevented during autoclave sterilization, so that the useful life of the endoscopic image pickup apparatus 3 can be prolonged.

Furthermore, although this is not particularly shown in the figures, it would also be possible to construct the endoscopic apparatus 1 as an electronic endoscope in which an image pickup element is disposed in the tip end portion of the long slender insertion part instead of the endoscope 2 and endoscopic image pickup apparatus 3.

A second embodiment of the present invention will be described with reference to FIGS. 7 and 8.

Note that constituent elements that are the same as those in the abovementioned first embodiment are labeled with the same symbols, and a detailed description of such elements will be omitted.

Figure 7:
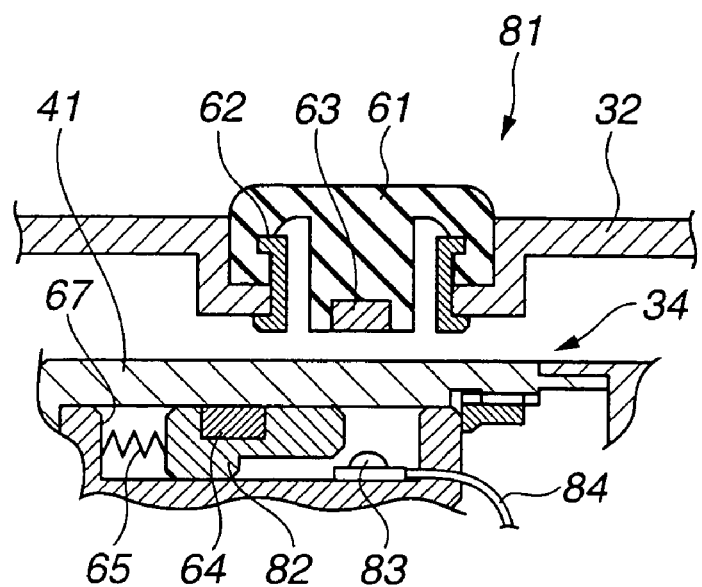
FIGS. 7 and 8 are figures that illustrate a second embodiment of the present invention.
Figure 8:
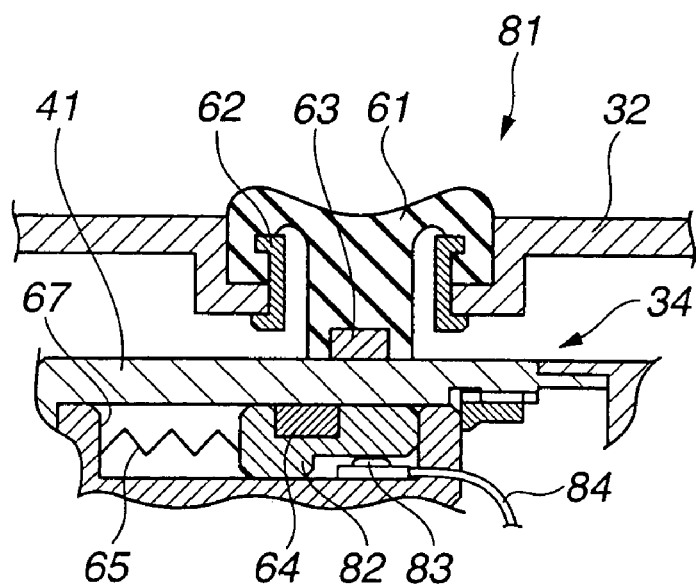

In the remote switch 81 of the present embodiment, as is shown in FIGS. 7 and 8, the shape of the moving member 82 is slightly altered compared to that of the moving member 50; furthermore, a switch 83 which is placed in a conductive state by being pressed is installed instead of the photo-interrupter 49. Accordingly, a switch harness 84 is installed instead of the photo-interrupter harness 66.

The remote switch 81 has a construction in which the switch 83 is pressed and placed in a conductive state as a result of the moving member 82 moving onto the upper part of the switch 83.

The operation of this remote switch 81 will be described next.

When the mechanism is changed from the state shown in FIG. 7 to the state shown in FIG. 8 in which the operating member 61 is pressed, a magnetic connecting force is generated between the operating part magnet 63 and the moving member magnet 64, so that the moving member 82 begins to move rightward along the plane of the page against the elastic force of the coil spring 65. Then, the moving member 82 is finally moved onto the upper part of the switch 83. As a result, the switch 83 is pressed and placed in a conductive state.

Consequently, a signal is output from the switch 83; this signal is transmitted to the video processor 5 via the switch harness 84, hermetic connector 43 (shown in FIG. 2), camera cable 11, plug 12 (shown in FIG. 1) and receptacle 13, and is processed, so that the brightness of the video processor 5 is increased by one step.

Subsequently, if an operation in which the operating member 61 is pressed is again performed, the brightness is further increased by one step by an operation similar to that described above.

Thus, since the switch 83 constituting the switching means is disposed inside the air-tight unit 34, deterioration of the switching means of the remote switch can be prevented during autoclave sterilization, so that an effect similar to that of the first embodiment can be obtained.

A third embodiment of the present invention will be described with reference to FIGS. 9 and 10.

Furthermore, constituent elements that are the same as those in the abovementioned first embodiment are labeled with the same symbols, and a detailed description of such elements will be omitted.

Figure 9:
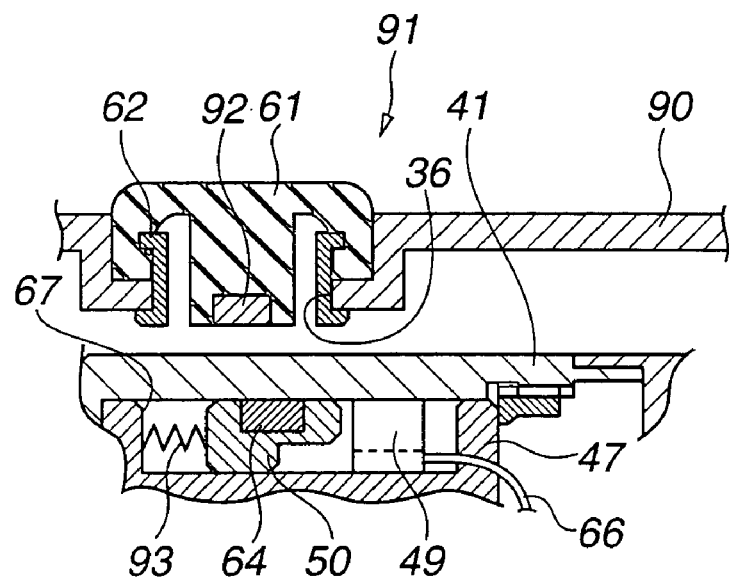
FIGS. 9 and 10 are figures that illustrate a third embodiment of the present invention.
Figure 10:
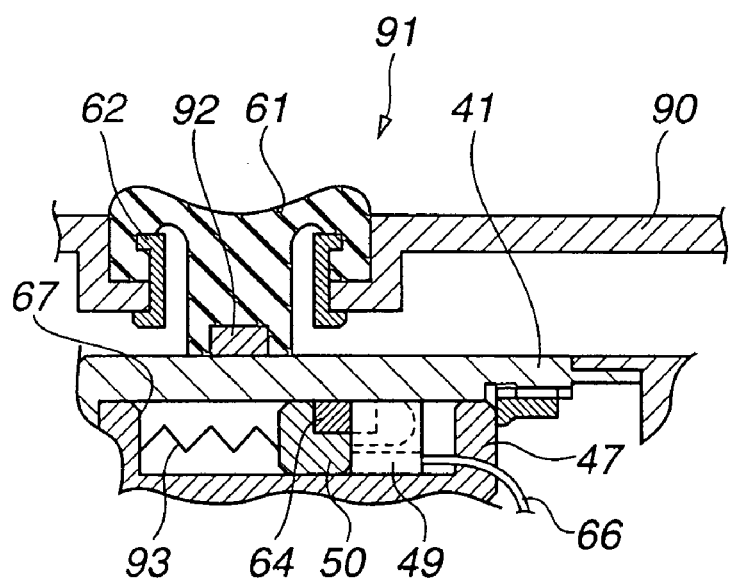

In the remote switch 91 of the present embodiment, as is shown in FIGS. 9 and 10, the operating part magnet 92 that constitutes the first magnet and the moving member magnet 64 are constructed such that (for example) the N poles of the two magnets are facing each other, thus generating magnetic forces that cause the two magnets to repel each other. Accordingly, the opening part 36 formed in the case body 90 into which the operating member 61 is inserted is formed on the side of the coil spring 93.

Furthermore, in order to move the moving member 50 in the direction of the photo-interrupter 49, the system may be devised so that the moving member magnet 64 is positioned closer to the photo-interrupter 49 than the operating part magnet 92 when the coil spring 93 is at its natural length.

Furthermore, as in the second embodiment, a construction may be used in which a switch 83 is installed instead of the photo-interrupter 49, and a switch harness 84 is installed instead of the photo-interrupter harness 66.

The operation of this remote switch 91 will be described next.

An operation is performed in which the operating member 61 is pressed as shown in FIG. 10 from the state shown in FIG. 9. Consequently, the moving member 50 begins to move rightward along the plane of the page against the elastic force of the coil spring 93 as a result of the repelling force generated between the operating part magnet 92 and the moving member magnet 64. Then, as is shown in the abovementioned FIG. 6, the moving member 50 finally moves into the area between the light-emitting part 71 and light-receiving part 72, so that a light-blocking state results.

As a result, a signal indicating that light is blocked between the light-emitting part 71 and light-receiving part 72 is output from the photo-interrupter 49. This signal that is output from the photo-interrupter 49 is transmitted to the video processor 5 via the photo-interrupter harness 66, hermetic connector 43 (shown in FIG. 2), camera cable 11, plug 12 (shown in FIG. 1) and receptacle 13, and is processed, so that the video processor 5 increases the brightness by one step.

Subsequently, if an operation in which the operating member 61 is pressed is again performed, the brightness is further increased by one step by an operation similar to that described above.

Thus, an effect similar to that of the first embodiment can also be obtained by using a construction in which the operating part magnet 92 and the moving member magnet 64 are constructed so that (for example) the N poles of the two magnets are like poles facing each other, thus causing the magnets to repel each other by their magnetic forces.

A fourth embodiment of the present invention will be described with reference to FIGS. 11 and 12.

Furthermore, constituent elements that are the same as those in the abovementioned first embodiment are labeled with the same symbols, and a detailed description of such elements will be omitted.

Figure 11:
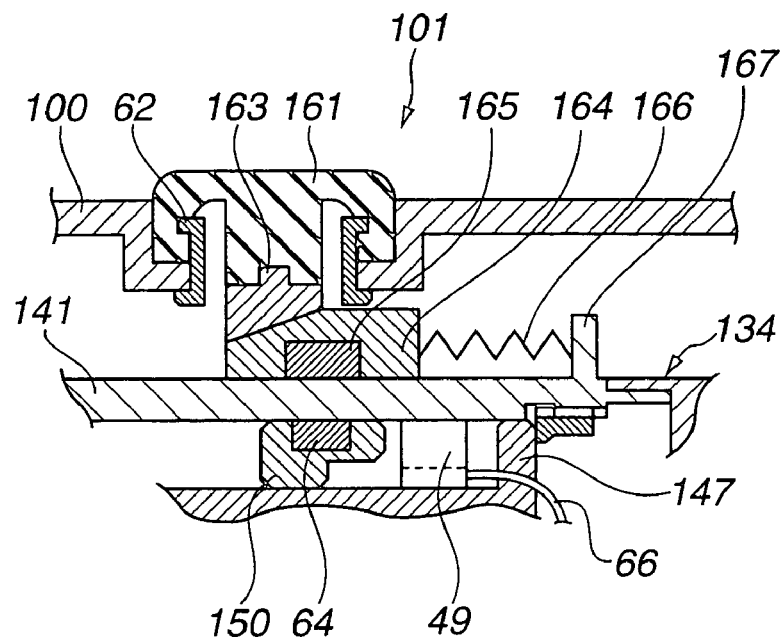
FIGS. 11 and 12 are figures that illustrate a fourth embodiment of the present invention.
Figure 12:
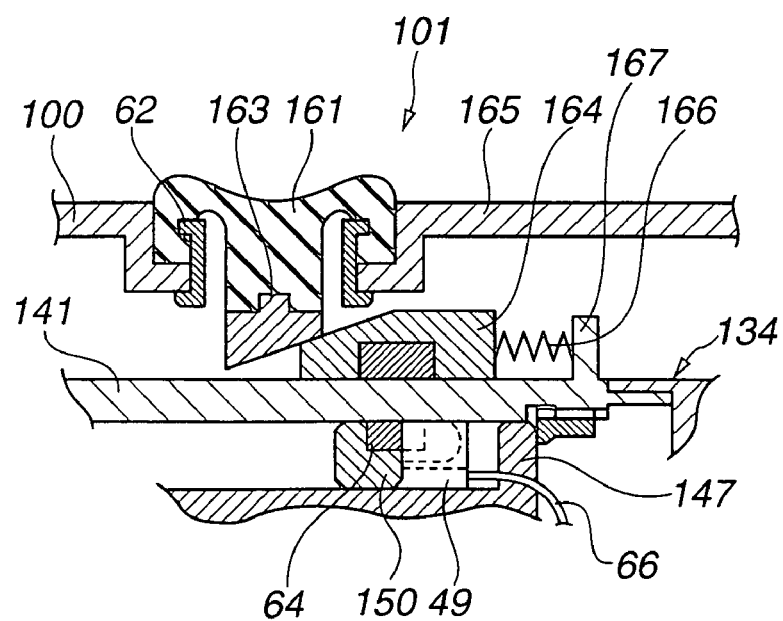

In the remote switch 101 of the present embodiment, as is shown in FIGS. 11 and 12, a hard pressing member 163 is formed as an integral part of the operating member 161.

Meanwhile, an intermediate body 164 used as an operating auxiliary member is disposed on the outside of the air-tight unit main body 141 of the air-tight unit 134 so that this intermediate body 164 slides over the outer circumferential surface of the air-tight unit main body 141. An intermediate body magnet 165 which constitutes a first magnet is formed as an integral part of this intermediate body 164. As a result, switching-function change-over means with respect to the photo-interrupter 49 is constituted.

The moving member 150 and photo-interrupter 49 are disposed in the gap between the air-tight unit main body 141 and the solid state image pickup element frame 147.

Furthermore, a coil spring 166 (for example) which biases the intermediate body 164 is disposed in this remote switch 101. One end of this coil spring 166 is fastened to the intermediate body 164, and the other end is fastened to the flange part 167 of the air-tight unit main body 141.

The coil spring 166 biases the intermediate body 164 so that the moving member 150 is caused to move in the direction that separates the moving member 150 from the photo-interrupter 49 by the magnetic connecting force of the intermediate body magnet 165 and moving member magnet 64.

In other words, the remote switch 101 is constituted by the operating member 161, pressing member 163, intermediate body 164, intermediate body magnet 165, coil spring 166, moving member 150, moving member magnet 64, photo-interrupter 49 and photo-interrupter harness 66.

Next, the operation of the remote switch 101 will be described.

An operation is performed in which the operating member 161 is pressed as shown in FIG. 12 from the state shown in FIG. 11. Consequently, the intermediate body 164 is caused to begin to move rightward along the plane of the page against the elastic force of the coil spring 166 by the pressing member 163. In this case, the moving member 150 is also caused to move rightward along the plane of the page by the magnetic connection between the intermediate body magnet 165 and the moving part magnet 64. Then, the moving member 150 finally moves into the area between the light-emitting part 71 and light-receiving part 72 as shown in FIG. 6, so that a light-blocking state results.

As a result, the photo-interrupter 49 outputs a signal indicating that light is blocked between the light-emitting part 71 and the light-receiving part 72. The signal that is output from this photo-interrupter 49 is transmitted to the video processor 5 via the photo-interrupter harness 66, hermetic connector 43 (shown in FIG. 2), camera cable 11, plug 12 (shown in FIG. 1) and receptacle 13, and is processed, so that the brightness of the video processor 5 is increased by one step.

Subsequently, if an operation in which the operating member 161 is pressed is again performed, the brightness is further increased by one step by an operation similar to that described above.

Thus, switching-function change-over means with respect to the photo-interrupter 49 is constituted by installing an intermediate body 164 with an integral intermediate body magnet 165 as an operating auxiliary member on the outside of the air-tight unit main body 141.

Furthermore, up to this point, an endoscopic image pickup apparatus with a straight shape has been described; however, the operating mechanism for a medical device of the present invention can also be applied to an L-shaped endoscopic image pickup apparatus of the type widely used in urology and the like.

Here, an example in which the present invention is applied to an L-shaped endoscopic image pickup apparatus will be described.

Figure 13:
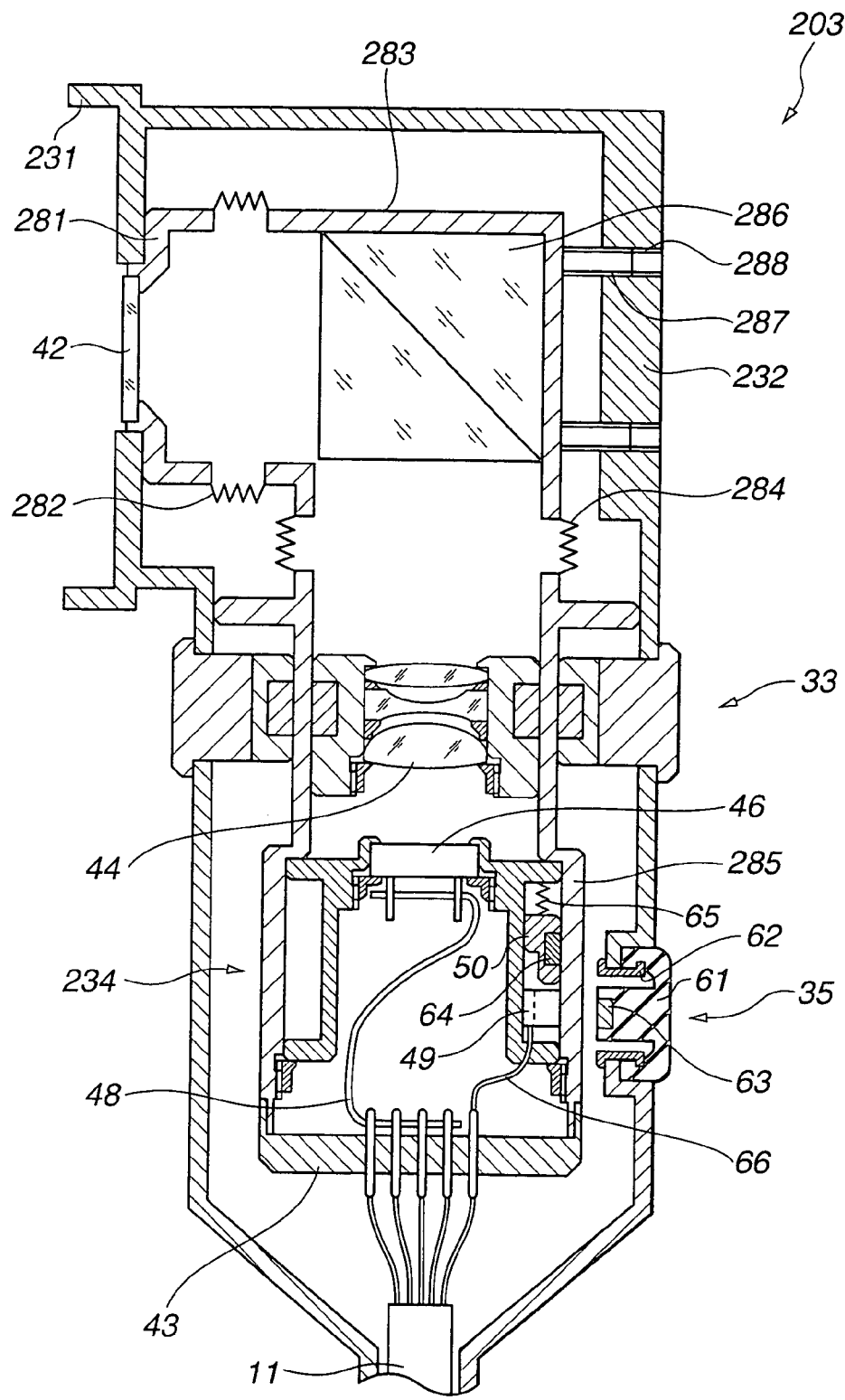
FIG. 13 is a sectional view of an endoscopic image pickup apparatus which illustrates a fifth embodiment of the present invention.

A fifth embodiment of the present invention will be described with reference to FIG. 13.

Furthermore, constituent elements that are the same as those in the abovementioned first embodiment are labeled with the same symbols, and a detailed description of such elements will be omitted.

As is shown in the figure, the L-shaped endoscopic image pickup apparatus 203 is constituted mainly by a scope mount 231, a case body 232, a focus adjustment part 33, an air-tight unit 234, a remote switch 35, a camera cable 11, and the plug 12 shown in FIG. 1.

The case body 232 is constructed in a shape in which the side of scope mount 231 is bent 90°.

The air-tight unit 234 is constituted by a cover glass 42, a cover glass frame 281, a first bellows part 282, a prism frame 283, a second bellows part 284, an air-tight unit main body 285 and a hermetic connector 43.

The cover glass frame 281 and prism frame 283 are joined air-tightly by the first bellows part 282. The prism frame 283 and air-tight unit main body 285 are joined air-tightly by the second bellows part 284.

Furthermore, the cover glass 42 is joined air-tightly to the end surface of the cover glass frame 281 to which the first bellows part 282 is not joined. The hermetic connector 43 is joined air-tightly to the end surface of the air-tight unit main body 285 to which the second bellows part 284 is not joined.

For example, a prism or a mirror 286 such as a Dach mirror that can bend the light path is fastened to the prism frame 283. Accordingly, the endoscopic images that are transmitted via the cover glass 42 are bent at substantially a right angle by this mirror 286, and are captured by the solid state image pickup element 46 via the optical system 44.

Furthermore, a plurality of adjustment screws 287 which are used to perform position adjustments such as adjustment of the inclination of the mirror 286 and the like are disposed in the endoscopic image pickup apparatus 203. These adjustment screws 287 can be moved in the direction of the optical axis by screw-engaging these screws with female screws 288 formed in the case body 232. The position of the mirror 286 can be adjusted by moving these adjustment screws 287 and pressing the prism frame 283.

Furthermore, in the endoscopic image pickup apparatus 203 that is formed in an L shape, the remote switch 35 is similar to that in the first embodiment. Accordingly, each time that the operating member 61 is pressed, the brightness of the video processor 5 is increased by one step. In other words, an effect similar to that of the first embodiment can be obtained in this endoscopic image pickup apparatus 203 as well.

Figure 14:
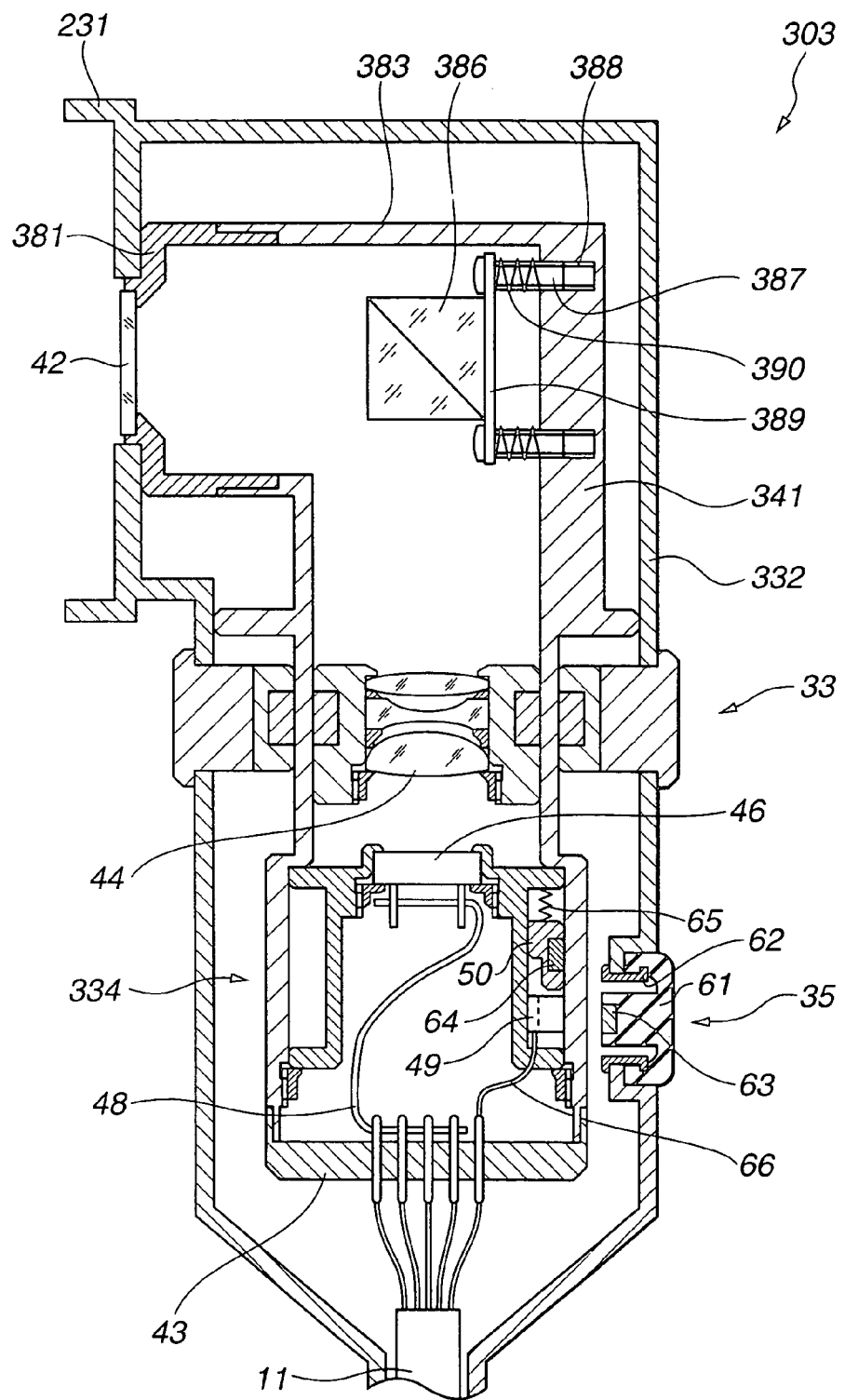
FIG. 14 is a sectional view of an endoscopic image pickup apparatus which illustrates a sixth embodiment of the present invention.

A sixth embodiment of the present invention will be described with reference to FIG. 14.

Furthermore, constituent elements that are the same as those in the abovementioned first through fifth embodiments are labeled with the same symbols, and a detailed description of such elements will be omitted.

As is shown in the figure, the L-shaped endoscopic image pickup apparatus 303 is constituted mainly by a scope mount 231, a case body 332, a focus adjustment part 33, an air-tight unit 334, a remote switch 35, a camera cable 11 and the plug 12 shown in FIG. 1.

The air-tight unit 334 is constituted by a cover glass 42, a cover glass frame 381, an air-tight unit main body 341 and a hermetic connector 43.

The side of the scope mount 231 of the case body 332 and air-tight unit main body 341 is bent 90°.

The cover glass frame 381 and air-tight unit main body 341 are joined air-tightly. Furthermore, the cover glass 42 is joined air-tightly to the end surface of the cover glass frame 381 to which the air-tight unit main body 341 is not joined. The hermetic connector 43 is joined air-tightly to the end surface of the air-tight unit main body 341 to which the cover glass frame 381 is not joined.

A mirror 386 is disposed in the corner part of the air-tight unit main body 341 that is bent 90°.

The mirror 386 is disposed on the inside of the air-tight unit main body 341. This mirror 386 is disposed on a mirror base 389. This mirror base 389 is held by adjustment screws 387 on which coil springs 390 are disposed. In other words, these coil springs 390 are disposed between the mirror base 389 and the air-tight unit main body 341.

For example, screw through-holes (not shown in the figure) are disposed in the four corners of the mirror base 389. A plurality of adjustment screws 387 are inserted into these screw through-holes, and these adjustment screws 387 are screw-engaged with female screws 388 formed in the air-tight unit main body 341. The female screws 388 do not pass entirely through the air-tight unit main body 341, but are formed to an intermediate point in the side wall of the air-tight unit main body 341.

The coil springs 390 provide a biasing force in the direction that opens the gap between the air-tight unit main body 341 and mirror base 389. Furthermore, the angle of the mirror 386 can be adjusted by adjusting the adjustment screws 387.

As a result of using this structure, the position of the mirror 386 can be adjusted by rotating the plurality of adjustment screws 387.

In the endoscopic image pickup apparatus 303 formed in an L shape, the remote switch 35 is similar to that in the first embodiment. Accordingly, each time that operating member 61 is pressed, the video processor 5 increases the brightness by one step. In other words, the same effect as that of the first embodiment can also be obtained in this endoscopic image pickup apparatus 303.

Meanwhile, in cases where an L-shaped endoscopic image pickup apparatus is used in urology or the like, the endoscopic image pickup apparatus may be used in an inclined state. In this case, there may be instances in which it is necessary to rotate the solid state image pickup element 46 so that this element is caused to coincide with the top and bottom on the monitor 6. An embodiment that handles this will be described below.

A seventh embodiment of the present invention will be described with reference to FIG. 15.

Furthermore, constituent elements that are the same as those in the abovementioned first through sixth embodiments are labeled with the same symbols, and a detailed description of such elements will be omitted.

The L-shaped endoscopic image pickup apparatus 403 shown in the figure has a rotating mechanism that rotates the solid state image pickup element 46.

The endoscopic image pickup apparatus 403 is constituted mainly by a scope mount 431, a case body 432, a focus adjustment part 33, an air-tight unit 434, a remote switch 35, an image pickup element rotating part 490, a camera cable 11 and the plug 12 shown in FIG. 1.

The image pickup element rotating part 490 is constituted by a rotating ring 491, a rotating ring magnet 492, a solid state image pickup element frame 447, an image pickup element frame magnet 493, a solid state image pickup element 46 and a printed board 494.

The rotating ring 491 is operated when the solid state image pickup element 46 is to be rotated. The outer circumferential surface of this rotating ring 491 is disposed so as to be rotatable in a state in which this surface is exposed from the case body 432.

The rotating ring magnet 492 is integrally disposed on a portion of the inner circumference of the rotating ring 491. The solid state image pickup element frame 447 holds the solid state image pickup element 46. The solid state image pickup element frame 447 is disposed so that this frame can rotate about the direction of the optical axis of the optical system 44 in a state in which this frame contacts the inner circumference of the air-tight unit main body 441.

The image pickup element frame magnet 493 is integrally disposed on a portion of the outer circumference of the solid state image pickup element frame 447. The image pickup element frame magnet 493 faces the rotating ring magnet 492 with the air-tight unit main body 441 interposed. This image pickup element frame magnet 493 and rotating ring magnet 492 form a magnetic connection. The printed board 494 is electrically connected to the solid state image pickup element 46, and is disposed on the base end of the solid state image pickup element 46.

Figure 16:
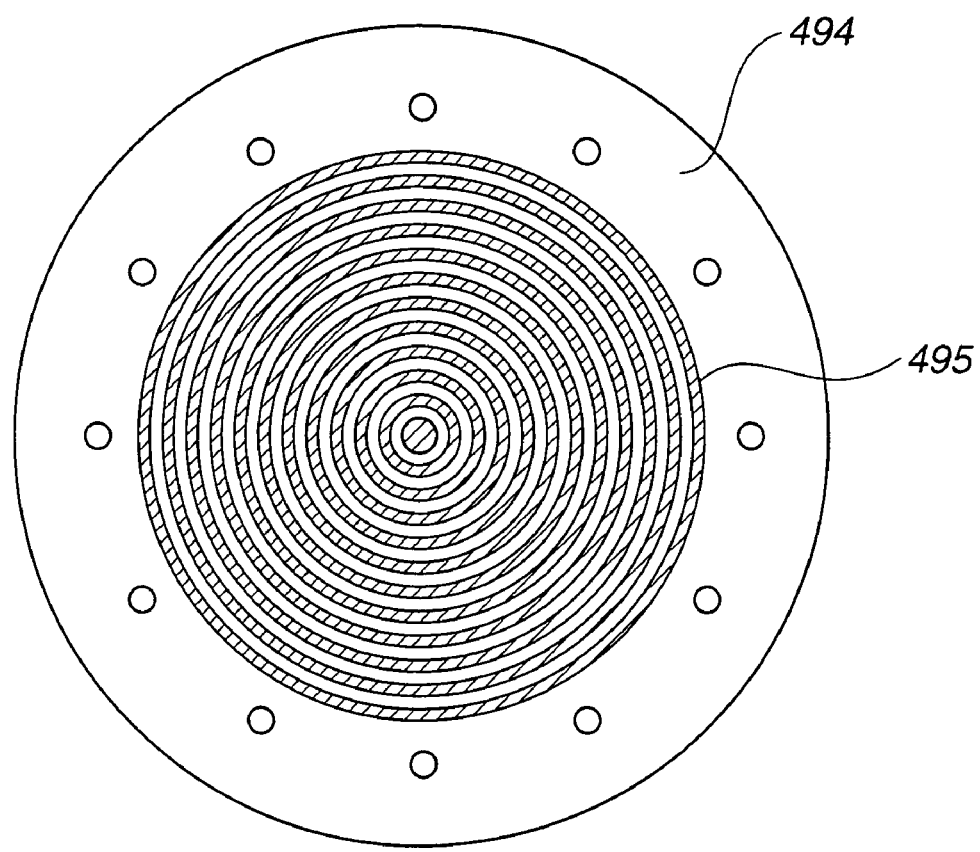

A plurality of patterns 495 formed in concentric circles as shown in FIG. 16 are disposed on this printed board 494.

Figure 15:
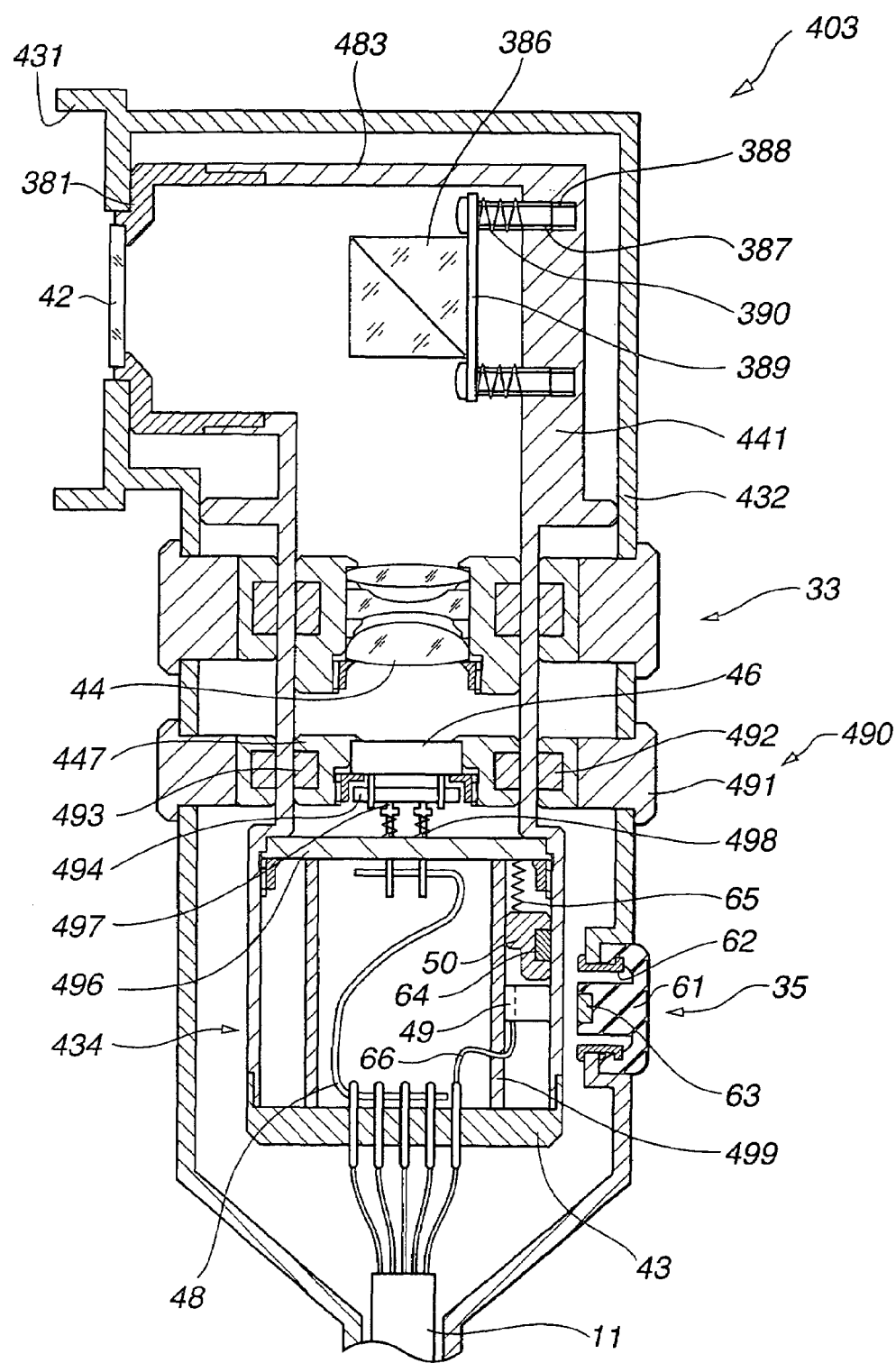
FIGS. 15 and 16 are figures that illustrate a seventh embodiment of the present invention.

As is shown in FIG. 15, contact pins 497 are disposed in a connector 496 so that these contact pins correspond to the patterns 495. For example, these contact pins 497 are biased toward the printed board 494 by coil springs 498 that are elastic bodies. As a result, the connector 496 is electrically connected to the plurality of patterns 495.

Furthermore, one end of the coil spring 65 of the remote switch 35 is fastened to the connector 496. A holding tube 499 is disposed on the rear side of the connector 496. The moving member 50 and photo-interrupter 49 of the remote switch 35 are disposed between the holding tube 499 and the air-tight unit main body 441.

Next, the operation of the endoscopic image pickup apparatus 403 will be described.

The rotating ring 491 of the endoscopic image pickup apparatus 403 is rotated. As a result, the solid state image pickup element 46 and printed board 494 fastened to the solid state image pickup element frame 447 are caused to rotate by the magnetic connection of the rotating ring magnet 492 and image pickup element frame magnet 493.

In this case, since the patterns 495 are disposed in the form of concentric circles, the patterns 495 and contact pins 497 are electrically connected regardless of the rotational position. Accordingly, the electrical signals of the endoscopic images captured by the solid state image pickup element 46 are transmitted to the video processor 5 via the printed board 494, connector 496, flexible board 48, hermetic connector 43, camera cable 11, plug 12 (shown in FIG.

1) and receptacle 13. In other words, the endoscopic images on the monitor 6 are also rotated.

Furthermore, in the endoscopic image pickup apparatus 403 that is formed in an L shape, the remote switch 35 is substantially the same as that in the first embodiment. Accordingly, each time that the operating member 61 is pressed, the video processor 5 increases the brightness by one step. In other words, the same effect as that of the first embodiment can also be obtained in this endoscopic image pickup apparatus 403.

Thus, the endoscopic images on the monitor 6 can be rotated by rotating the rotating ring 491.

Figure 17:
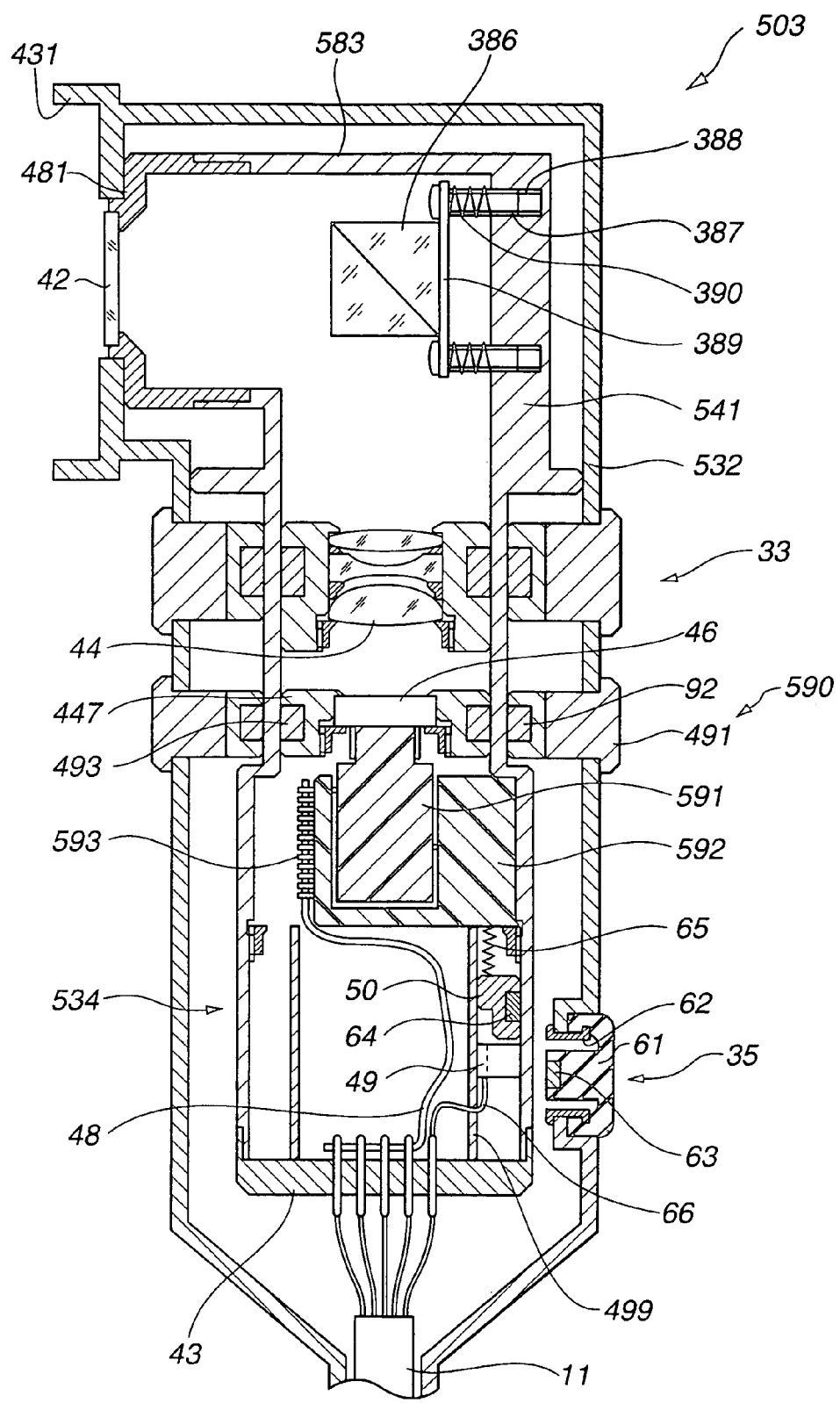
FIGS. 17 through 19 are figures that illustrate an eighth embodiment of the present invention.

An eighth embodiment of the present invention will be described with reference to FIGS. 17 through 19.

Furthermore, constituent elements that are the same as those in the abovementioned first through seventh embodiments are labeled with the same symbols, and a detailed description of such elements will be omitted.

The L-shaped endoscopic image pickup apparatus 503 shown in the figure has a rotating mechanism that rotates the solid state image pickup element 46.

The endoscopic image pickup apparatus 503 is constituted mainly by a scope mount 431, a case body 532, a focus adjustment part 33, an air-tight unit 534, a remote switch 35, an image pickup element rotating part 590, a camera cable 11 and the plug 12 shown in FIG. 1.

The image pickup element rotating part 590 is constituted by a rotating ring 491, a rotating ring magnet 492, a solid state image pickup element frame 447, an image pickup element frame magnet 493, a solid state image pickup element 46 and a first resin member 591.

The first resin member 591 is electrically connected to the solid state image pickup element 46, and is disposed on the base end of the solid state image pickup element 46. A second resin member 592 is disposed on the outer circumference of this first resin member 591 so as to cover the first resin member 591.

Figure 18:
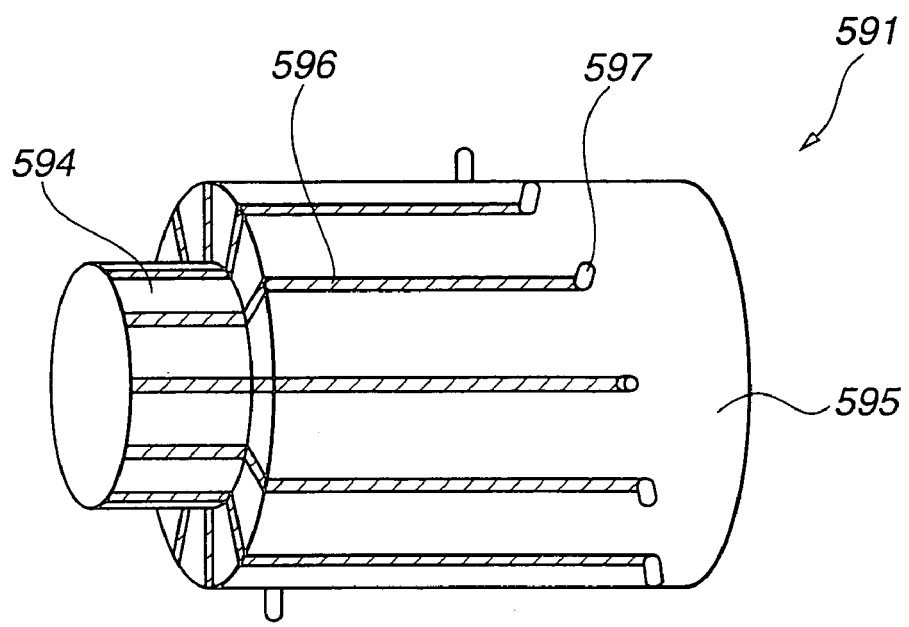

As is shown in FIG. 18, the first resin member 591 has a small-diameter part 594 and a large-diameter part 595. The small-diameter part 594 is formed on the side of the solid state image pickup element 46. A plurality of first patterns 596 of different lengths are formed on the first resin member 591 by (for example) three-dimensional wiring or the like. These first patterns 596 are formed from the small-diameter part 594 to the large-diameter part 595. Protruding contact parts 597 are formed on the ends of the plurality of first patterns 596 located on the side of the large-diameter part 595. These contact parts 597 possess elasticity.

Figure 19:
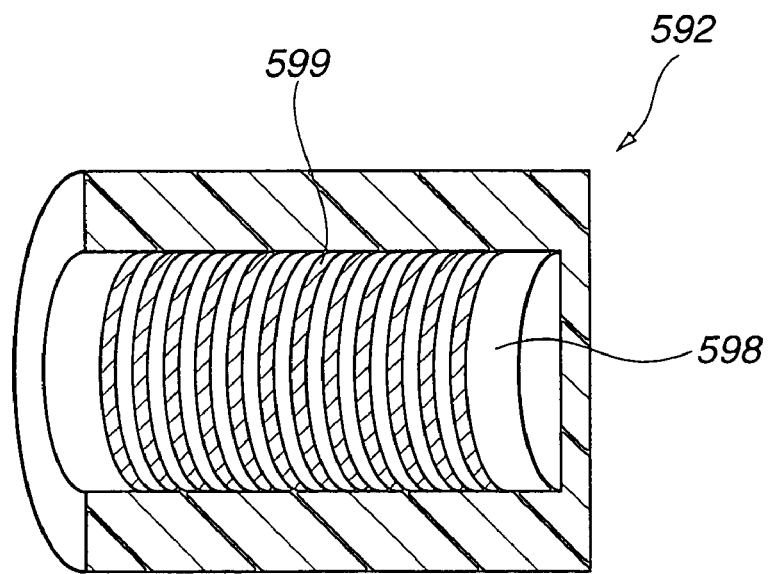

As is shown in FIG. 19, second patterns 599 are formed around the entire circumference on the inner circumferential surface 598 of the second resin member 592. These second patterns 599 are formed in positions that correspond to the contact parts 597 shown in FIG. 18. Furthermore, the contact pins 593 shown in FIG. 17 are disposed on the outer surface of this second resin member 592. The flexible board 48 is attached to the contact pins 593. The contact pins 593 and second patterns 599 are electrically connected via throughholes not shown in the figures.

One end of the coil spring 65 is fastened to the second resin member 592. Furthermore, the moving member 50 and photo-interrupter 49 are disposed between the holding tube 499 and air-tight unit main body 541.

Next, the operation of the endoscopic image pickup apparatus 503 will be described.

The rotating ring 491 of the endoscopic image pickup apparatus 503 is rotated. As a result, the solid state image pickup element 46 and first resin member 591 fastened to the solid state image pickup element frame 447 are caused to rotate by the magnetic connection of the rotating ring magnet 492 and image pickup element frame magnet 493.

In this case, since the second patterns 599 are formed over the entire circumference of the second resin member 592, the contact parts 597 and second patterns 599 are electrically connected regardless of the rotational position of the first resin member 591.

Accordingly, the electrical signals of the endoscopic images captured by the solid state image pickup element 46 are transmitted to the video processor 5 via the first patterns 596, contact parts 597, second patterns 599, contact pins 593, flexible board 48, hermetic connector 43, camera cable 11, plug 12 (shown in FIG. 1) and receptacle 13. Consequently, the endoscopic images on the monitor 6 rotate.

Furthermore, in endoscopic image pickup apparatus 503 that is formed in an L shape, the remote switch 35 is substantially the same as that in the first embodiment. Accordingly, each time that the operating member 61 is pressed, the video processor 5 increases the brightness by one step. In other words, the same effect as that of the first embodiment can also be obtained in this endoscopic image pickup apparatus 503.

Thus, by rotating the rotating ring 491, it is possible to rotate the endoscopic images on the monitor 6 in the same manner as in the seventh embodiment.

A ninth embodiment of the present invention will be described with reference to FIGS. 20 through 22.

Furthermore, constituent elements that are the same as those in the abovementioned first through eighth embodiments are labeled with the same symbols, and a detailed description of such elements will be omitted.

In the present embodiment, a construction in which an operating member 602 that constitutes a remote switch 601 slides through the opening part 636 of the case body 632 is used instead of a remote switch that is operated by pressing.

In concrete terms, the remote switch 601 is constituted mainly by a photo-interrupter 49, a moving member 50, an operating member 602, an operating part magnet 603 that constitutes a first magnet, a moving member magnet 64, a coil spring 65 (for example) that constitutes biasing means, and a photo-interrupter harness 66.

The operating member 602 is constructed so that this member slides in the direction of the optical axis over the outer circumferential surface of the air-tight unit main body 641. The operating part magnet 603 is integrally disposed on the side of the surface of this operating member 602 that contacts the outer circumferential surface of the air-tight unit main body 641. This operating part magnet 603 faces the moving member magnet 64 with the air-tight unit main body 641 interposed.

Figure 22:
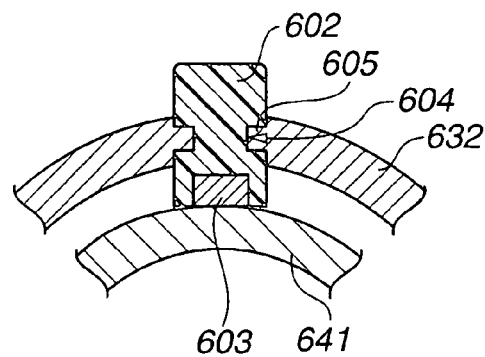

Furthermore, as is shown in FIG. 22, a recessed part 604 is formed in the operating member 602, and a protruding part 605 is formed in the case body 632, so that the operating member 602 is prevented from falling out of the case body 632.

Next, the operation of the remote switch 601 will be described.

Figure 20:
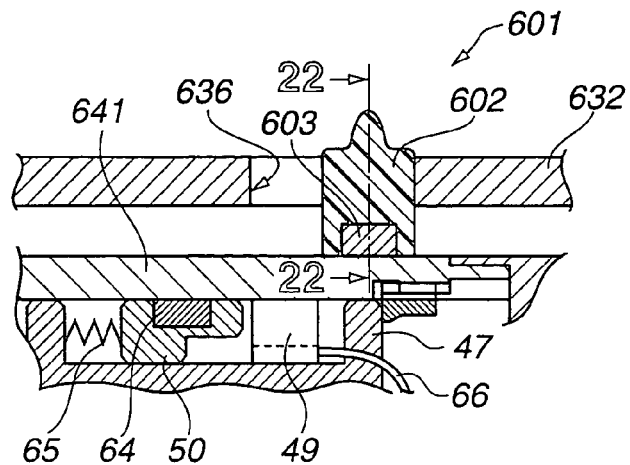
FIGS. 20 through 22 are figures that illustrate a ninth embodiment of the present invention.
Figure 21:
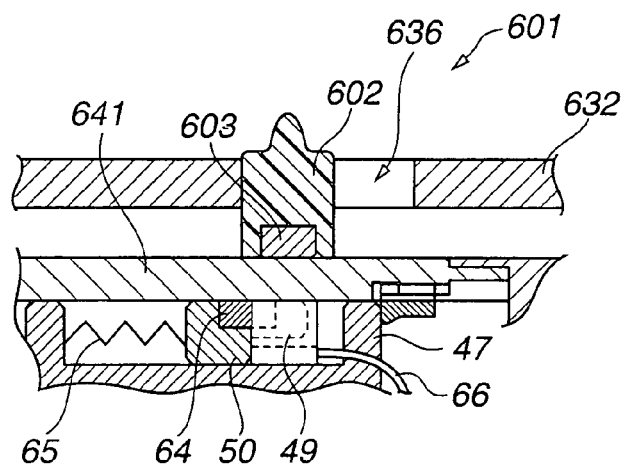

The operating member 602 is caused to slide as shown in FIG. 21 from the state shown in FIG. 20. As a result, the moving member 50 is caused to begin to move rightward along the plane of the page against the elastic force of the coil spring 65 by the magnetic connection between the operating part magnet 603 and moving member magnet 64. Then, the moving member 50 finally enters the area between the light-emitting part 71 and light-receiving part 72 of the photo-interrupter 49 as shown by the broken line in FIG. 21 and as shown in FIG. 6, so that a light-blocking state results.

As a result, the photo-interrupter 49 outputs a signal which indicates that light is blocked between the light-emitting part 71 and light-receiving part 72. The signal that is output from this photo-interrupter 49 is transmitted to the video processor 5 via the photo-interrupter harness 66, hermetic connector 43 (shown in FIG. 2), camera cable 11, plug 12 (shown in FIG. 1) and receptacle 13, and is processed, so that the brightness of the video processor 5 is increased by one step.

Subsequently, if an operation in which the operating member 61 is pressed is again performed, the brightness is further increased by one step by an operation similar to that described above.

Thus, an effect similar to that of the first embodiment can be obtained even in cases where the construction of the operating member 602 that constitutes the remote switch 601 is, altered from a pressing type to a sliding type.

Furthermore, in the present embodiment, a photo-interrupter 49 is used in the sliding type remote switch 601; however, it would also be possible to construct the remote switch 601 by installing a switch 83 that is placed in a conductive state by being pressed instead of the abovementioned photo-interrupter 49.

Furthermore, the operating mechanisms for a medical device shown in FIGS. 1 through 22 are not limited to an endoscopic image pickup apparatus; these mechanisms can also be applied to various other types of medical devices such as electrical scalpels, ultrasonic endoscopes and the like.

Furthermore, in the operating mechanisms for a medical device shown in FIGS. 1 through 22, the biasing means biases the moving member directly; however, it would also be possible to use a construction in which a connecting member is disposed between the biasing means and the moving member, so that the biasing means biases the moving member indirectly.

Having described the preferred embodiments of the invention referring to the accompanying drawings, it should be understood that the present invention is not limited to those precise embodiments, and various changes and modifications thereof could be made by one skilled in the art without departing from the spirit or scope of the invention as defined in the appended claims.

What is claimed is:

1. An operating mechanism for a medical device, the operating mechanism comprising:
   a switching unit operable to designate an operation of the medical device;
   an air-tight unit configured to accommodate the switching unit air-tightly;
   a moving member disposed inside the air-tight unit, and movable between a position in which the switching unit designates the operation and a position in which the switching unit designates no operation;
   a biasing unit configured to directly or indirectly bias the moving member from the position in which the switching unit designates the operation to the position in which the switching unit designates no operation;
   an operating member disposed on an outside of the air-tight unit, and comprising an elastic portion deformable in accordance with a user operation; and
   a switching-function change-over unit adapted to move the moving member by magnetic force into the position in which an operation is designated against the biasing force of the biasing unit in accordance with an elastic deformation of the elastic portion caused by the user operation of the operating member.

2. The operating mechanism for a medical device according to claim 1, wherein the switching unit is a photo-interrupter.

3. The operating mechanism for a medical device according to claim 1, wherein the switching unit is a switch that is placed in a conductive state by being pressed.

4. The operating mechanism for a medical device according to claim 1, wherein the switching-function change-over unit comprises:
   a first magnet disposed on the operating member or an operating auxiliary member disposed on the outside of the air-tight unit with an air-tight unit main body interposed; and
   a second magnet disposed on the moving member disposed on the inside of the air-tight unit with the air-tight unit main body interposed.

5. The operating mechanism of claim 1, wherein the medical device, wherein the medical device is adapted to be sterilized at high-pressure in an autoclave.

6. An operating mechanism for a medical device comprising:
   a switch positioned inside an endoscope unit of the medical device and operable to control an operation in the endoscope unit;
   an air-tight unit that can accommodate the switch air-tightly;
   a moving member disposed inside the air-tight unit, the moving member operable to move between a position designating the operation and a position designating no operation;
   a biasing unit operative to bias the moving member from the position in which the switch designates the operation to the position in which the switch designates no operation;
   an operating member disposed outside of the air-tight unit, the operating member operable by an operator, and positioned such that no contact is made with the moving member, the operating member comprising an elastic portion elastically deformable in accordance with a user operation;
   a switching-function change-over portion operable to control the switch by varying the position of the moving member in accordance with elastic deformation of the elastic portion caused by the user operation of the operating member by exerting a magnetic force on the moving member in opposition to the biasing force of biasing unit.

7. The operating mechanism for a medical device according to claim 6, which further comprises a biasing member that directly or indirectly biases the moving member to the position designating no operation.

8. The operating mechanism for a medical device according to claim 6, wherein the switching-function change-over portion comprises:
   a first magnet which is disposed on the operating member or an operating auxiliary member disposed on the outside of the air-tight unit with an air-tight unit main body interposed; and
   a second magnet which is provided on the moving member disposed on the inside of the air-tight unit with the air-tight unit main body interposed.

9. The operating mechanism for a medical device according to claim 6, wherein the switch is a photo-interrupter.

10. The operating mechanism for a medical device according to claim 6, wherein the switch is placed in a conductive state by being pressed.

11. An operating mechanism for a medical device comprising:

switching means for controlling an operation of an endoscope unit of the medical device positioned inside the endoscope unit;

an air-tight unit that can accommodate the switching means air-tightly;

a moving member disposed inside the air-tight unit, the moving member for moving between a position designating the operation and a position designating no operation;

biasing means for biasing the moving member from the position in which the switching means designates the operation to the position in which the switching means designates no operation;

operating means positioned on the outside of the air-tight unit, the operating means operable by an operator, and disposed such that no contact is made with the moving member, the operating member comprising an elastic portion elastically deformable in accordance with a user operation; and switching-function change-over means for varying the position of the moving member to switch the functional operation designated by the switching means of the endoscope unit, the switching-function change-over means varying the position of the moving member by exerting a magnetic force in opposition to the biasing force of the biasing means, in accordance with elastic deformation of the elastic portion caused by the user operation.

12. The operating mechanism for a medical device according to claim 11, wherein the switching-function change-over means comprise:

a first magnet which is disposed on an operating member or an operating auxiliary member disposed on the outside of the air-tight unit with an air-tight unit main body interposed; and a second magnet which is disposed on the moving member disposed on the inside of the air-tight unit with the air-tight unit main body interposed.

13. The operating mechanism for a medical device according to claim 11, wherein the switching means is a photo-interrupter.

14. The operating mechanism for a medical device according to claim 11, wherein the switching means is a switch that is placed in a conductive state by being pressed.

* * * * *

UNITED STATES PATENT AND TRADEMARK OFFICE
CERTIFICATE OF CORRECTION

PATENT NO. : 7,278,965 B2  Page 1 of 1
APPLICATION NO. : 10/789200
DATED : October 9, 2007
INVENTOR(S) : Masami Shimizu It is certified that error appears in the above-identified patent and that said Letters Patent is hereby corrected as shown below:

IN THE CLAIMS:

Claim 5, column 16, line 19, after "The operating mechanism of claim 1" delete "wherein the medical device, wherein the medical device".

Claim 5, column 16, line 19, after "The operating mechanism of claim 1" insert -- including the medical device which --.

Claim 8, column 16, line 55, after "The operating mechanism for a medical device according to" delete "claim 6" and insert -- claim 7 --.

Claim 11, column 17, line 26, after "position of the moving member to switch the" delete "functional".

Signed and Sealed this

Twenty-seventh Day of May, 2008

JON W. DUDAS
*Director of the United States Patent and Trademark Office*